United States Patent [19]

Bloxom, Jr.

[11] Patent Number: 4,804,373
[45] Date of Patent: Feb. 14, 1989

[54] STRUCTURE TO INTRODUCE IRRIGATION LIQUID THROUGH A STOMA OF AN OSTOMY PATIENT

[76] Inventor: Ingrid B. Bloxom, Jr., P.O. Box 357, Wicomico, Va. 23184

[21] Appl. No.: 205,621

[22] Filed: Jun. 2, 1988

Related U.S. Application Data

[63] Continuation of Ser. No. 935,779, Nov. 28, 1986, abandoned.

[51] Int. Cl.⁴ .............................................. A61M 31/00
[52] U.S. Cl. ..................................... 604/277; 604/334
[58] Field of Search ..................... 285/9.2; 604/27, 48, 604/264–267, 275–277, 334

[56] References Cited

U.S. PATENT DOCUMENTS

| | | | |
|---|---|---|---|
| 737,795 | 9/1903 | Van't Woud. | |
| 1,676,308 | 7/1928 | Wood | 604/41 |
| 2,412,531 | 12/1946 | Pape | 285/9.2 |
| 2,482,361 | 9/1949 | Parrigin | 604/276 |
| 2,664,088 | 12/1953 | Hoch | 604/275 |
| 3,830,235 | 8/1974 | Marsan | 604/277 |
| 3,910,274 | 10/1975 | Nolan | 604/333 |
| 3,990,448 | 11/1976 | Mather | 604/275 |
| 4,050,461 | 9/1977 | Ruby | 604/277 |

Primary Examiner—Stephen C. Pellegrino
Assistant Examiner—J. L. Kruter
Attorney, Agent, or Firm—John Cyril Malloy

[57] ABSTRACT

A device or structure for the introduction of irrigating liquid into the intestine through a stoma or any applicable opening in the body of a patient wherein intestinal irrigation to stimulate fecal evacuation is required. The subject device is further structured to include a primary passage as well as a plurality of secondary channels to insure that fluid communication is established between the interior of the intestine and a fluid channelling conduit which in turn may be connected to a supply or irrigating liquid and a monitoring device for the determination of sufficient peristaltic action in the intestine indicating the introduction of a sufficient amount of irrigating liquid to establish fecal discharge.

1 Claim, 1 Drawing Sheet

STRUCTURE TO INTRODUCE IRRIGATION LIQUID THROUGH A STOMA OF AN OSTOMY PATIENT

This a continuation of application Ser. No. 6/935,779 filed 11/28/86 now abandoned.

BACKGROUND OF THE INVENTION

1. Field of the Invention

The present invention relates to a device partially designed to introduce irrigating liquid into the intestine of anostomy patient through a surgically formed stoma and also structured to establish fluid communication between the interior of the intestine and a conduit which initially directs irrigating fluid to the intestine through the stoma and attached fluid introducing device. The establishment of fluid communication allows the determination of sufficient peristaltic action in the intestine to indicate stoppage of the introduction of irrigating liquid thereto.

2. Description of the Prior Art

Colonic irrigation is a well-known medical treatment, not only in the case of conventional enemas through the anus end of the rectum, but also in the case of irrigation through surgically provided openings, known as stomas, into other parts of the colon, as in the case of colostomy and ilestomy patients. In all of these cases, the degree of discomfort and length of ordeal in irrigating the colon to the extent of discharging fecal matter from the colon is significant. Although varying in particular cases, it is particularly disagreeable for those requiring irrigation directly into the colon through the surgically provided stoma. Such stomas are formed from the end of a shortened colon after the end has been drawn up through the abdominal wall and outer skin.

Equipment to introduce irrigation liquid into the colon of an ostomy patient is disclosed, for example, in U.S. Pat. No. 3,830,235 to Marsan. Such equipment conventionally includes a bag for the irrigation liquid, a flexible tube to convey liquid from the bag to a device through which the liquid is introduced into the colon, a clip to shutoff the flow to the tube, and a discharge device to catch the backflow of fecal matter, etc. when the fluid introducing device is removed from the stoma. The subject inventor has recognized has recognized that the discomfort and time required for colonic or olher intestinal irrigation is minimized by detecting the buildup of peristaltic action of the intestine in response to injection of irrigating liquid and, importantly, the termination of the injection or supply of irrigating liquid when there is an indication of sufficient peristaltic action to provide the desired evacuation without the aid of additional liquid. Such prompt termination of the introduction of irrigating liquid has the further important advantage of preventing an excessively large amount of liquid introduced into the intestine from suppressing the peristaltic action initiated by the smaller amount of liquid initially introduced.

In order to determine the establishment of sufficient peristaltic action to cause evacuation of the intestine, a monitoring device, in various embodiments, has been utilized by the present inventor to determine the requisite amount of peristaltic action and provide an indication to stop the introduction of irrigating liquid into the intestine. However, in order for the peristaltic action to be propery monitored, fluid communication has to be established and maintained between the interior of the intestine and the monitoring device. In addition, a liquid flow has to be first established between a supply of irrigating liquid and the interior of the intestine.

Fluid introducing devices known in the prior art are generally formed to protrude into the intestinal area through the stoma to a point of actual engagement with the intestine wall. Due to obvious flexibility of the intestine and the surrounding stoma collar, a passage or path of introduction of the fluid through the device into the intesine is sometimes blocked causing a failure of an adequate supply of irrigating liquid to the intestine or the prevention of peristaltic action from being properly monitored through a backflow of fluid to the aforementioned monitoring device. In light of these problems there is a need in this area for an introduction device capable of providing an efficient and reliable supply of irrigating fluid to the intestine and at the same time establishing and maintaining fluid communication between the interior of the intestine and any type of monitoring device associated with the supply or channelling conduit directing the irrigating liquid to the introduction device.

SUMMARY OF THE INVENTION

The present invention is directed towards a device for introducing irrigating fluid into the interior of an intestine primarily through a surgically formed stoma or alternately through a natural opening of the body. Also the device is specifically structured to establish and maintain reliable fluid communication between the interior of the intestine and montoring device which may be attached to a liquid channelling conduit initially directing the irri9ating liquid to the device and therethrough into the interior of the intestine.

The subject device may be more commonly referred to as "stoma cone" and in a preferred embodiment may include a substantially conical configuration having a first end defining what may be generally referred to as the apex of the conical configuration. This first end is, when applied to the stoma or opening in the body, inserted into the interior of the intestine in registry therewith. The opposite end of the body protrudes exteriorly from the stoma or body orifice and includes an at least partially hollow interior portion. A primary passage is integrally formed to extend through the body and be opened at its opposite end. More specifically, one open end of the primary passage is aligned with the first end of the body on the interior of the intestine while the opposite end of the passage is in direct communication and exits at the hollow interior portion of the body. Further, the interior open end of the primary passage is specifically configured to recieve or be connected in fluid communication with a fluid channelling conduit. Such conduit is connectable to a supply of irrigating liquid and also may be secured to a monitoring device. The existence of the monitoring device is operative on the basis of determining the creation of peristaltic action in the intestine sufficient to begin evacuation thereof. In turn the determination of such peristaltic action is based on the establishment and maintenance of fluid communication between the interior of the intestine and the monitoring device itself.

The subject stoma cone differs from prior art introduction devices at least in part by the creation of a plurality of spaced apart channels integrally formed in the body and communicating at an interior end of each such channels with the primary passage at a point along its length spaced from the first end of the body. In addition, each channel extends angularly outward from the primary passage and terminates on the exterior surface of the body in an open end. Accordingly, the plurality of secondary channels in effect create secondary lines of fluid communication leading from the interior of the intestine to the primary passage at a location spaced from the open end of the primary passage positioned on the interior of the intestine. This insures that fluid communication between the interior of the intestine and the fluid channelling conduit attached to the opposite end of the primary passage will always be maintained to enable the determination of peristaltic action in the intestine. This is true even when the open end of the primary passage within the intestine is inadvertently covered or blocked due to coming into en9agement with the intestine wall. Fluid communication will be established through any one or more of the unblocked secondary channels and a length of the primary passage extending inwardly from the open end of the primay passage, presumably blocked by the intestine wall, and the end of the liquid channelling conduit secured to the interior end of the primary passage.

The invention accordingly comprises the features of construction, combination of elements and arrangement of parts which will be exemplified in the construction hereinafter set forth, and the scope of the invention will be indicated in the claims.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
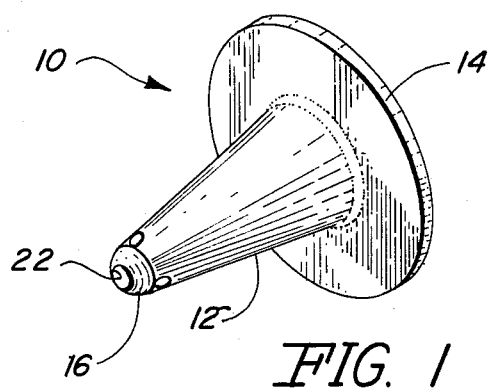
FIG. 1 is an isometric view of the device of the present invention.
Figure 2:
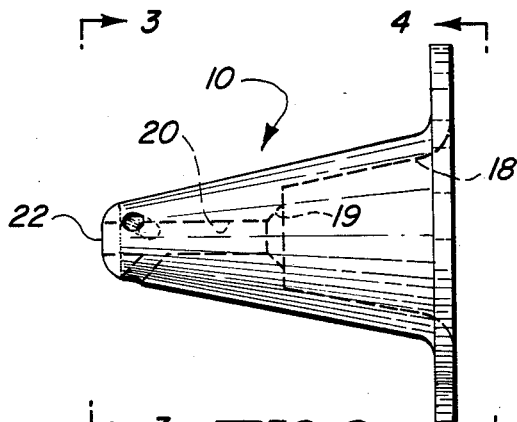
FIG. 2 is a side elevation of the embodiment of FIG. 1 with interior structural details represented in phantom lines.
Figure 3:
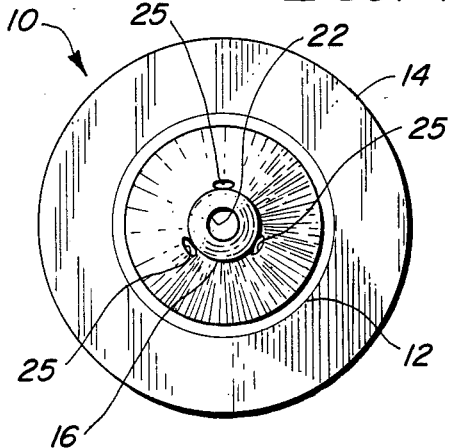
FIG. 3 is an end elevational along line 3—3 of FIG. 2.
Figure 4:
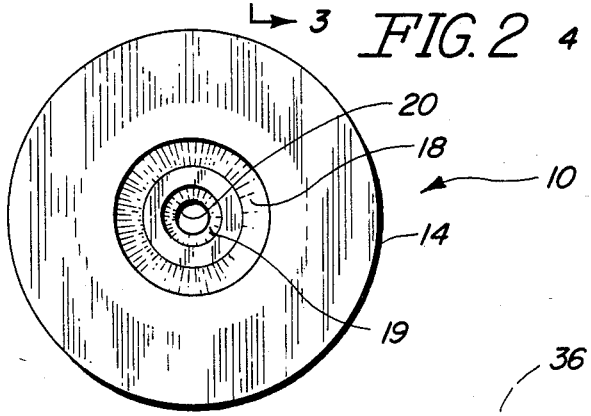
FIG. 4 is an opposite end elevation along line 4—4 of FIG. 2.
Figure 5:
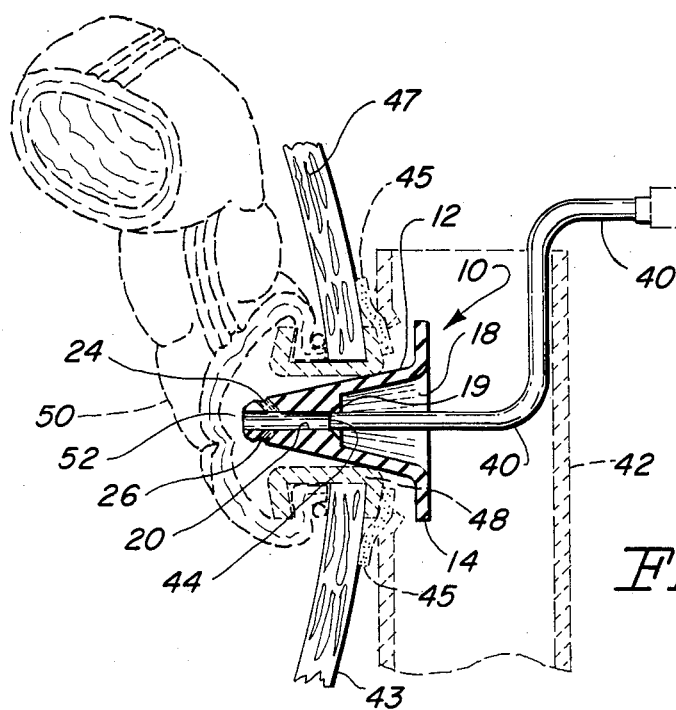
FIG. 5 is a sectional view of the subject device as applied to a stoma and intestine to be irrigated and being connected to a supply of irrigating liquid through a liquid channelling conduit, certain components of this view being represented in phantom lines.

As shown in FIGS. 1 through 5, the present invention relates to a fluid introduction device generally indicated as 10 and known in the medical field as a "stoma cone." The device 10 includes an outwardly extending main body portion 12 generally formed into a conical configuration terminating at a first end 16 and at an opposite end in the form of a flange 14. The end 16 may generally define what can be referred to as the apex of the conical configuration of body 12 and, as shown in FIG. 5, has a curved outer surface and is disposed on the interior of the patient, more specifically, within the interior 52 of the intestine 50, to be described in greater detail hereinafter. With reference to FIGS. 1 and 5, the body 12 includes an at least partially hollow interior portion 18 opening at the undersurface of the flange 14 (see FIG. 4) and extending inwardly into the interior of the body 12 where it terminates at a junction or socket 19 defining an interior open end of a primary passage 20. The open interior proximal end or junction 19 is specifically configured and disposed to receive and allow connection thereto of a fluid channelling conduit 40 (see FIG. 5) also to be described in greater detail hereinafter.

The primary passage 20 terminates at an oppositely disposed open inner end 22 again which exits or communicates with the interior space 52 of the intestine 50 to be irrigated. The end or flange 14 remains exteriorly of the patient or abdominal wall 47 and is specifically applied by being extended through the stoma generally represented in FIG. 5 in phantom lines. The shape of the stoma has its configuration maintained somewhat by a collar 43 and an annular connector 45 serves to secure the collar to the exterior skin surface of the abdominal wall 47. Accordingly, in its operative position the first end 16 of the device 10 is disposed o the interior of the intestine as at 52 and therefore establishes fluid communication by the existence of the passage 20 and the open position of the open end 22 with the fluid handling conduit 40 connected to the interior proximal end 19 as at the correspondingly positioned end 44 of conduit 40.

An important feature of the present invention is the existence of a plurality of channels 24, 26 and 28 disposed in spaced relation to one another and each terminating on the outer surface of the body 12 adjacent the open end 22 and first end 16 of the primary passage 20 and body 12 respectively. More specifically, the open ends 25, 27 and 29 define openings also communicating with the interior 52 of the intestine 50 wherein the opposite ends of the respective channels 24, 26 and 28 intersect with and are in fluid communication with the passage 20 along a portion of its length spaced from the end 22. Accordingly, alternate fluid passages between the interior 52 of the intestine 50 and the conduit 40 are established in the event that the end 22 of the primary passage 20 is closed or blocked due to inadvertent engagement or at least partial collapse of the interior surface or wall of the intestine over such opening 22. It is extremely unlikely, due to the wide, spaced apart displacement of the open ends 25, 27 and 29 as well as the channels 24, 26 and 28 respectively that each of the open ends, as set forth above, as well as the open end 22 of the primary passage will in fact be blocked by an inadvertent closure or blocking of the interior surface of the intestine wall. In a preferred embodiment of the present invention, each of the channels 24, 26, and 28 are angled outwardly to the exterior surface of the body 12. Also in a preferred embodiment, each of these channels are disposed at an angle of substantially 45° to the central longitudinal axis of passage 20.

Therefore, as long as at least one of such openings are in fact efl unblooked, flow of irrigating fluid from a supply 32 through connecting conduit 39, and a monitoring device 38 and finally through fluid channelling conduit 50 into the interior of the intestine 50 as at 52 can be accomplished by flow through the primary passage or alternately anyone or all of the secondary channels 25, 26 and 28. Further, and importantly, fluid communication will be maintained between the interior of the intestine 50 and the monitoring device 38, when such is used, for the purpose of determining the establishment of sufficient peristaltic action in the intestine to accomplish evacuation thereof. Other features associated with the device 10 but not considered per se a part of the invention herein include a support stand 34, having an upper end properly shaped to engage and support a fastening member 36 contained on the supply means 30 which may be in the form of a container 32 holding the irrigating liquid contained therein as shown. Once sufficient peristaltic action has been established within the intestine 50 to allow for evacuation thereof, the device 10 is removed from the stoma and from its operative position as shown in FIG. 5 through a discharge device 42 for evacuation and discharge of the fecal matter through the stoma into the discharge device 42.

Now that the invention has been described,

What is claimed is:

1. A device for introducing irrigating liquid into an intestine through a stoma at which time the intestine may be prolapsed, said device comprising in combination, a stoma cone, an irrigating liquid conduit having both a distal and a proximal end means for connection to a irrigation liquid supply; a liquid supply; a monitoring device means located up stream of said cone to sense peristaltic action in the intestine; said cone having.

an axially symmetrical cone-shaped exterior body having (a) a smooth exterior surface, (b) a smoothly rounded apex, (c) a base, and (d) a longitudinal extending said axis axial primary passageway through said cone-shaped body, said rounded apex being sized to insert into the mouth of a stoma with the smooth exterior surface in sealing engagement with the stoma mouth, said axial passageway being enlarged through a longitudinal portion extending from the base toward the apex, said axial portion being sized and configured to snugly receive said distal end of the liquid conduit in fluid communication with the primary passageway at a zone between the apex and the base, and said passageway being of reduced cross-sectional area between the zone and the apex, and a plurality of at least three equianuglary spaced, equisized, secondary passageways extending axially and inwardly from the said cone exterior surface at a common axial location proximate the rounded apex and in fluid communication with the primary passageway between the apex and said zone, said cone shaped body, source of irrigating fluid, said conduit and said monitoring device in serial fluid communicated with one another through one of said secondary passageways to the intestine even if the intestine is in a prolapsed condition so that liquid can flow from said liquid supply through said monitoring device and sense any resulting peristaltic action.

* * * * *